United States Patent
Hancock

(10) Patent No.: US 6,306,116 B1
(45) Date of Patent: Oct. 23, 2001

(54) METHOD AND APPARATUS FOR PRESSURIZING THE RIGHT ATRIUM OR RIGHT VENTRICLE TO ASSIST CARDIAC FUNCTION DURING BEATING HEART SURGERY

(75) Inventor: David E. Hancock, San Francisco, CA (US)

(73) Assignee: Origin Medsystems, Inc., Menlo Park, CA (US)

( * ) Notice: Subject to any disclaimer, the term of this patent is extended or adjusted under 35 U.S.C. 154(b) by 0 days.

(21) Appl. No.: 09/410,487

(22) Filed: Sep. 30, 1999

(51) Int. Cl.$^7$ ...................................................... A61M 5/00
(52) U.S. Cl. ................................ 604/101.01; 604/101.03; 604/118; 604/101.04; 600/18
(58) Field of Search ................................ 600/16, 17, 18; 604/8, 9, 7, 27, 30, 35, 43, 93.01, 96.01, 101.01, 101.03, 118, 119, 101.04

(56) References Cited

U.S. PATENT DOCUMENTS

| | | | |
|---|---|---|---|
| 5,267,940 | * 12/1993 | Moulder | 600/16 |
| 5,711,753 | * 1/1998 | Pacella et al. | 600/16 |
| 5,980,448 | * 11/1999 | Heilman et al. | 600/16 |
| 6,045,496 | * 4/2000 | Pacella et al. | 600/16 |

* cited by examiner

Primary Examiner—Anhtuan T. Nguyen
Assistant Examiner—Jennifer Maynard

(74) Attorney, Agent, or Firm—Girard & Equitz LLP

(57) ABSTRACT

A method and apparatus for pressurizing the right atrium or right ventricle of a beating heart during surgery to assist cardiac function. The apparatus has an intake tube for insertion in the inferior or superior vena cava, a return tube for insertion in the right atrium or right ventricle, and a pump (e.g., a peristaltic pump). In operation, blood is pumped from the vena cava into an intake port of the intake tube, from the intake tube through the pump to the return tube, and from the return tube to the right atrium or right ventricle. Optionally, a balloon mounted around the intake tube's distal end is inflated to center the intake port in the vena cava and provide a pressure bulkhead. The pump preferably pumps blood in one direction from an input port to an output port. Alternatively, the intake and return tubes are branches of a single Y-tube, and the pump has one port coupled to the tube and a two-stage operating cycle: a stage which draws blood in from the tube through the port; and a stage which returns the blood in the opposite direction through the port to the tube. Preferably, the apparatus includes a return manifold (through which the intake tube passes) at the distal end of the return tube. The return manifold defines a chamber which is in fluid communication with the return tube and defines one or more outflow ports. Blood returning from the pump flows through the return tube into the manifold chamber. Preferably, an atrial pressure sensor measures the pressure of blood pumped into the right atrium, the sensor output is provided to a control unit, and the pump's stroke volume is controlled in response to the measured pressure.

7 Claims, 4 Drawing Sheets

METHOD AND APPARATUS FOR PRESSURIZING THE RIGHT ATRIUM OR RIGHT VENTRICLE TO ASSIST CARDIAC FUNCTION DURING BEATING HEART SURGERY

FIELD OF THE INVENTION

The invention pertains to a method and apparatus for pumping blood (from one or both of the superior and inferior vena cava) into the right atrium or right ventricle of a beating heart. Typically, the apparatus is used to assist the cardiac function of a beating heart during surgery thereon.

BACKGROUND OF THE INVENTION

Coronary artery bypass grafting (CABG) has traditionally been performed with the use of a cardiopulmonary bypass (CPB) machine to oxygenate and perfuse the body during surgery. Recently, techniques have been developed to allow for performing CABG without the use of CPB by stabilizing the epicardial surface of a beating heart at the coronary anastomotic site with a stabilizer (e.g., stabilizing feet) to allow placement of sutures through the graft vessel and recipient coronary artery. This procedure may be performed through a partial or full sternotomy, or via a thoracotomy (which is an incision between two adjacent ribs).

A challenge to beating heart surgery is that some hearts do not tolerate the necessary manipulation (e.g., movement of the beating heart into position for surgery and stabilization of the site on which surgery is performed) well from a hemodynamic standpoint. Currently, when the beating heart is lifted or twisted (to access the portion thereof on which surgery will be performed), the cardiac output drops, often to dangerously low levels.

There is a need for a pumping apparatus capable of assisting the beating heart during surgery, to compensate for decreased hemodynamic function (including decreased ventricular function) that results from manipulation. The inventive pumping apparatus is designed to perform this function.

Some pumping systems have been used to assist the beating heart during surgery. However, such conventional systems are subject to significant limitations and disadvantages.

For example, pumps (such as the Medtronic "Bio-Pump" centrifugal pump available from Medtronic, Inc.) have been used to pump blood from the vena cava during beating heart surgery. It has been proposed to use a system including such a pump (and an intake cannula and outflow cannula connected to the pump) as follows: the intake cannula is inserted into the vena cava, the outflow cannula is inserted into the pulmonary artery, and blood is then pumped through the cannulae from the vena cava and back into the pulmonary artery during surgery. However, this technique requires two incisions in the patient: one to allow insertion of the intake cannula in the vena cava; the other in the pulmonary artery to allow insertion of the outflow cannula therein. Undesirably, the latter incision must be made in a high pressure zone (the pulmonary artery).

As another example, the Hemopump Cardiac Assist System (sponsored by Medtronic, Inc.) includes a cannula for insertion through an incision in the ascending aorta into the left ventricle of a beating heart. The cannula includes (and encloses) a pump. The pump is a rotating Archimedes screw whose intake is the distal end of the cannula (which is positioned in the left ventricle) and whose outlet is positioned in the ascending aorta. In use, the pump continuously pumps blood from the left ventricle into the aorta. However, this apparatus assists the left heart, rather than the right heart (which is weaker than the left heart). The apparatus does not inflate the right atrium or right ventricle, and thus does not provide the hemodynamic benefits which result from inflation of the right atrium or right ventricle during beating heart surgery.

SUMMARY OF THE INVENTION

In a class of embodiments, the inventive apparatus includes an intake tube (for insertion into the inferior vena cava or superior vena cava), a return tube (for insertion into the right atrium or right ventricle), and a pump coupled between the intake and return tube. In operation, blood is pumped from the vena cava into an intake port of the intake tube, from the intake tube (through the pump) to the return tube, and from the return tube to the right atrium or right ventricle. Preferably, the pump is configured to pump blood from the vena cava into at least one intake port of the intake tube, from the intake tube to the return tube, and from the return tube to the right atrium or right ventricle. Preferably, a balloon is mounted around the distal end of the intake tube near the intake port, and the balloon is inflated when the intake port has been inserted into the vena cava in order to prevent backflow and resultant pressure loss during the systolic phase of the heart beat (and preferably also to center the intake port in the vena cava).

Preferably, the pump has an input port coupled to the intake tube and an output port coupled to the return tube, and is configured to pump blood in one direction (from input port to output port, and thus from intake tube to return tube). A peristaltic pump is an example of such a pump. Alternatively, the intake and return tubes are branches of a single Y-tube, the pump has one port coupled to the tube, and the pump has two-stage cycle: a first stage in which it draws blood in from the tube through the pump's port; and a second stage in which it returns blood from within the pump, back through the pump's port in the opposite direction to the tube.

Preferably, the apparatus includes a return manifold at the distal end of the return tube, and the intake tube extends through the return manifold. The return manifold defines a chamber that is sealed from the intake tube (but is in fluid communication with the return tube) and is perforated by one or more outflow ports, the outflow ports being positioned so that blood can flow into the right atrium (or right ventricle) through them when the intake tube's intake port is positioned in the vena cava. Blood returning from the pump flows through the return tube into the return manifold's chamber. Since the returning blood in the chamber is at high pressure, it flows out of the chamber's outflow ports (or port) into the right atrium or right ventricle. The returned blood flows from the right atrium into the right ventricle (or from the right ventricle to beyond the right ventricle), as occurs in normal functioning of a beating heart.

Preferably, the apparatus includes an atrial pressure sensor which measures the pressure of the blood which has flowed into the right atrium from the pump. In preferred implementations of such embodiments, the output of the sensor is provided to a control unit for the pump, and the stroke volume of the pump is controlled in response to the measured pressure to achieve a desired time-varying atrial pressure (a desired atrial pressure as a function of time). A typical stroke volume is less than 20 cc (but the optimal stroke volume may be greater in some applications).

In preferred embodiments, the intake port of the inventive apparatus is positioned (during use) in the inferior vena cava. In alternative embodiments, the intake port is positioned in the superior vena cava, or the inventive apparatus has a Y-shaped distal end having two intake ports, each of which is positioned in a different one of the inferior vena cava and the superior vena cava during use.

In other embodiments, the invention is a method for pressurizing the right atrium of a beating heart during surgery (to assist cardiac function). One example of such surgery is a coronary bypass grafting procedure on the beating heart. The method includes the steps of: (a) inserting a distal portion of an intake tube into at least one of the inferior vena cava and superior vena cava so that at least one intake port (defined by the distal portion of the intake tube) is positioned to receive blood from at least one of the inferior vena cava and the superior vena cava, and inserting a distal portion of a return tube into the right atrium or right ventricle so that at least one return port (defined by the distal portion of the return tube) is positioned to permit blood flow from the return tube into the right atrium (or right ventricle); and (b) pumping blood from the at least one intake port, through the intake tube and the return tube, and from the return tube to the right atrium (or right ventricle) through the at least one return port. Preferably, step (a) includes the step of inserting the distal portion of the intake tube into the inferior vena cava so that an intake port is positioned to receive blood from the inferior vena cava, and the method also includes the step of: (c) before step (b), but after the distal portion of the intake tube is inserted in the inferior vena cava, inflating a balloon around the distal portion of the intake tube to center the intake port in the inferior vena cava. Also preferably, step (b) includes the step of pumping the blood in one direction only (preferably in a peristaltic manner), from an input pump port coupled to the intake tube to an output pump port coupled to the return tube. Alternatively, the intake tube and the return tube are branches of a single Y-tube, step (b) is performed using a pump having a single pump port coupled to the Y-tube, and step (b) includes the steps of pumping the blood in a two-stage cycle, said cycle including the steps of: pumping a portion of the blood which has entered the Y-tube from said at least one intake port into the pump (in a first direction through the pump port); and then returning said portion of the blood from the pump, back through the pump port in a direction opposite to the first direction to the Y-tube (to cause at least some of the returned blood to flow into the return tube).

The invention functions to assist the beating heart during surgery, to compensate for decreased hemodynamic function (including decreased ventricular function) that results from manipulation. When the beating heart is lifted or twisted (to access the portion on which surgery will be performed), the cardiac output tends to drop (often to dangerously low levels) unless assisted in accordance with the invention. Assisted pressurizing of the right atrium or right ventricle in accordance with the invention is believed to increase the stroke volume of the other cardiac chambers, thus compensating for the decrease in ventricular function believed to be the cause of cardiac output drop during heart manipulation.

DETAILED DESCRIPTION OF THE PREFERRED EMBODIMENTS

A preferred embodiment of the invention will be described with reference to FIGS. 1–3.

Figure 1:
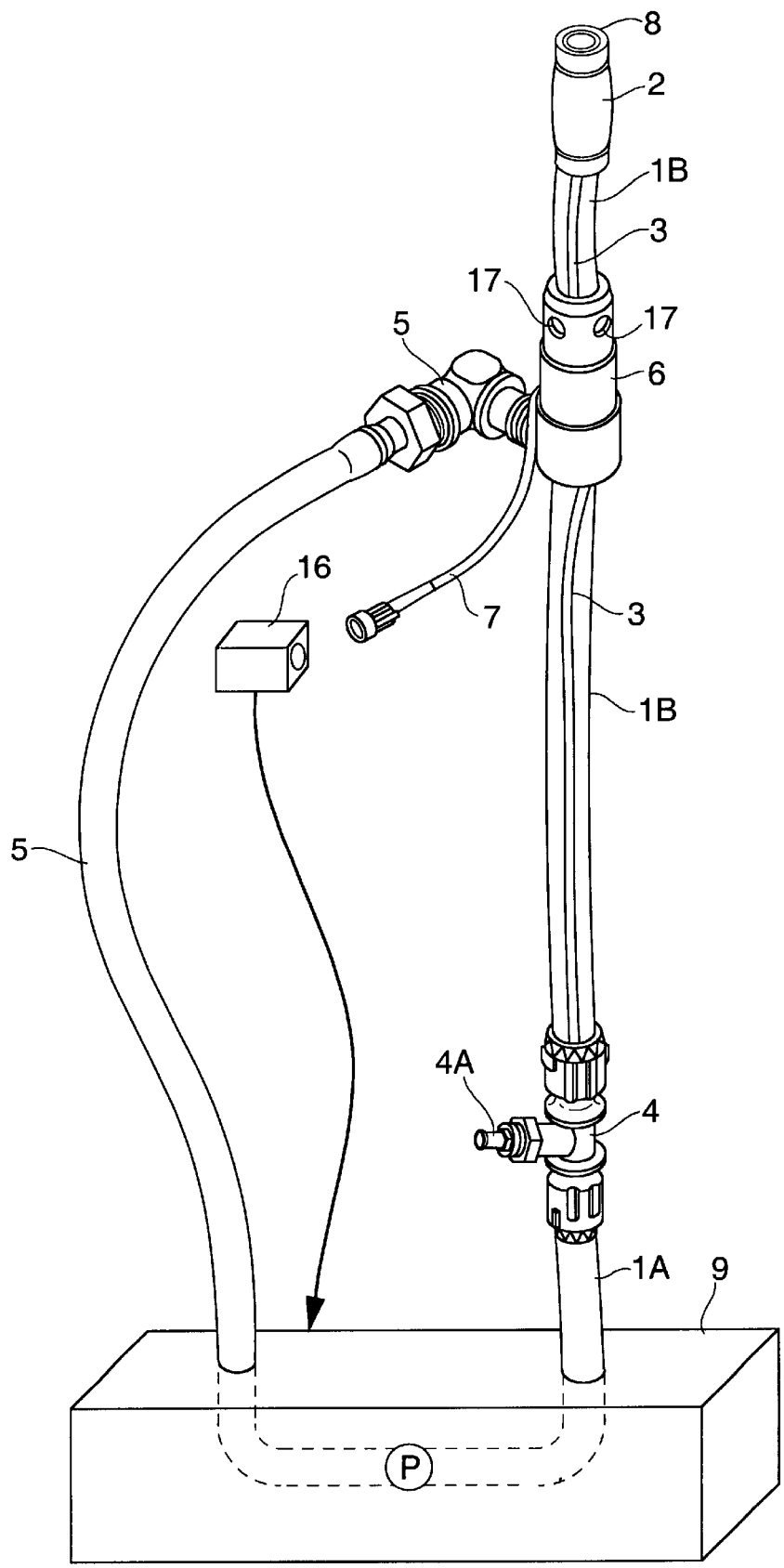
FIG. 1 is a perspective view of a preferred embodiment of the inventive apparatus.
Figure 2:
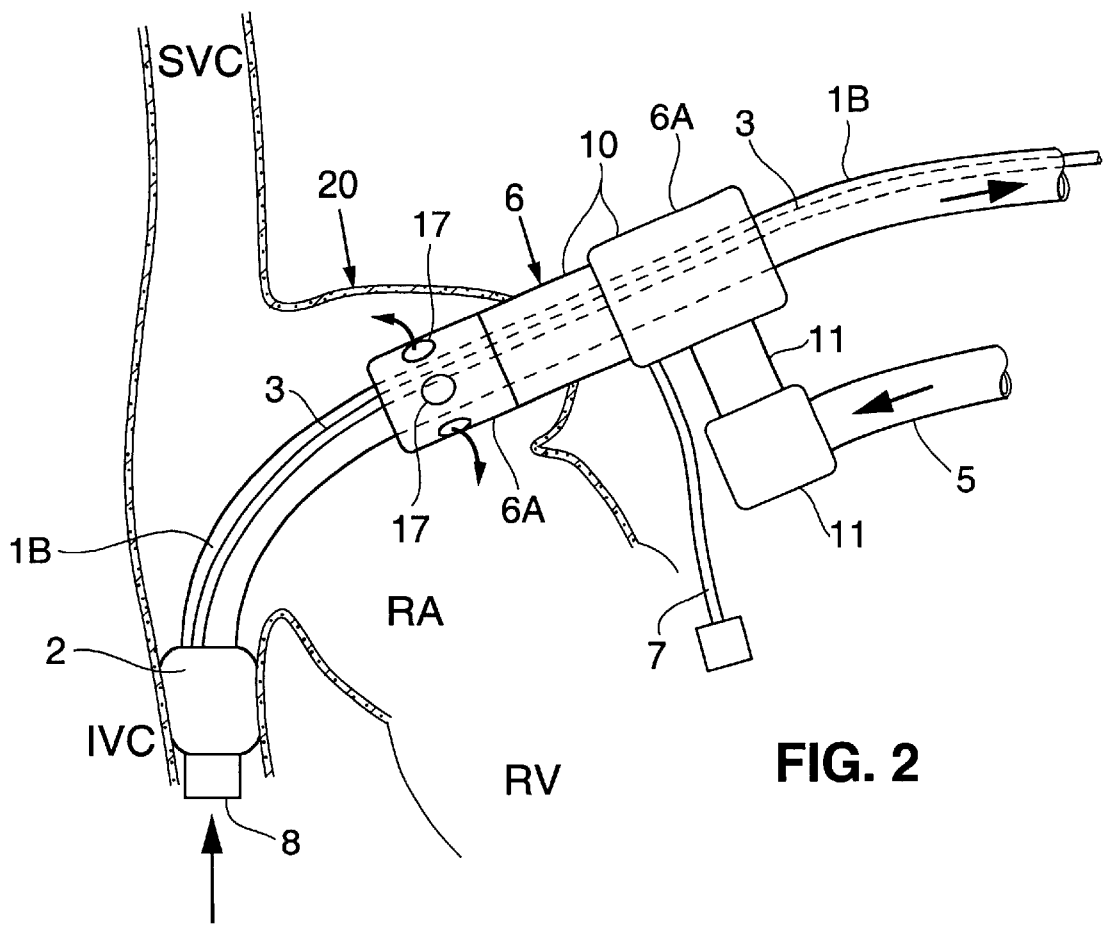
FIG. 2 is a simplified perspective view of a portion of the FIG. 1 embodiment of the inventive apparatus, elements of which are positioned in the right atrium and inferior vena cava of a patient (the atrium and vena cava are viewed in cross-section).
Figure 3:
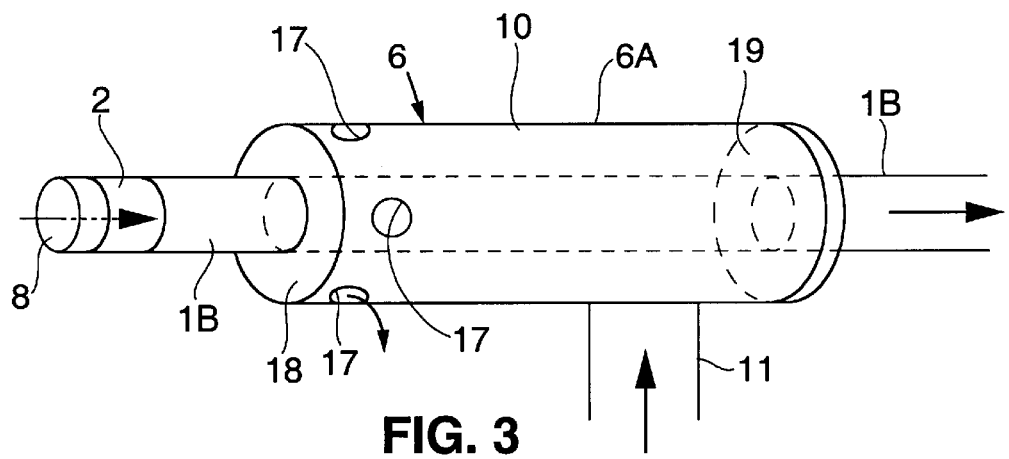
FIG. 3 is a perspective view of a portion of the FIG. 1 embodiment of the inventive apparatus.

The apparatus of FIGS. 1–3 is designed to assist the cardiac function of heart 20 (shown in FIG. 2) while heart 20 beats during surgery thereon. In use, intake port 8 is inserted into the inferior vena cava ("IVC") as shown in FIG. 2 (or alternatively, into the superior vena cava (labeled "SVC" in FIG. 2). Pump 9 draws blood from the vena cava into port 8, through an intake tube (comprising tubes 1A and 1B), and returns the blood through tube 5 (and fitting 11 and manifold 6) into the right atrium (labeled "RA" in FIG. 2) of heart 20.

With reference to FIG. 1, the intake tube of the apparatus comprises a length of tubing 1A (connected to an input port of pump 9), a length of tubing 1B, and fitting 4 connected between tubes 1A and 1B. Balloon 2 (having a toroidal inflated shape) is mounted around the outside of tube 1B (near tube 1B's distal end). Fitting 4 defines a balloon inflation fluid-introducing port 4A.

Balloon inflation tube 3 defines a lumen which extends through tube 1B from port 4A, and through an orifice in the wall of tube 1B (the orifice is under balloon 2 and thus not visible in FIG. 2) into fluid communication with the interior of balloon 2 (so that fluid can be introduced into port 4A through tube 3 for inflating balloon 2 when desired, and then withdrawn from the balloon out through port 4A).

Figure 8:
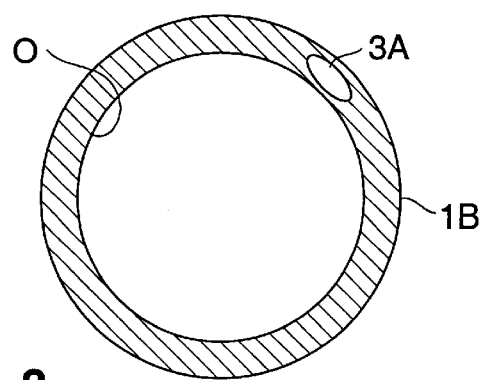
FIG. 8 is a cross-sectional view of an implementation of tube 1B (of FIGS. 1 and 2) whose side wall defines a balloon inflation lumen.

Preferably, the inventive apparatus is configured to define such a balloon inflation lumen without extending a tube through the interior volume enclosed by tube 1B, since the resulting irregularly shaped surface to which the blood is exposed may generate clot (or otherwise damage the blood). For example, a balloon inflation tube (which replaces tube 3 of FIGS. 1 and 2) can be positioned so as to extend outside tube 1B (i.e., along the outer cylindrical surface of tube 1B) from port 4A to balloon 2. Or, balloon inflation tube 3 is replaced by a lumen (e.g., lumen 3A of FIG. 8) which is defined by and extends within the side wall of tube 1B. For example, as shown in FIG. 8, the side wall of tube 1B (which has generally annular cross-section and surrounds central orifice O) is formed so as to define lumen 3A. Lumen 3A extends from port 4A to balloon 2, and runs parallel to the axis of orifice O).

The balloon inflation lumen (which may or may not be defined by a balloon inflation tube distinct from tube 1B) allows inflation fluid to be supplied to balloon 2 to inflate the balloon (to the inflated configuration shown in FIG. 2) when intake port 8 (at the distal end of tube 1B) has been inserted into the vena cava, in order to prevent backflow of blood during systol (by providing a pressure bulkhead between the right atrium and the inferior vena cava), and to center the intake port 8 in the vena cava while the inventive apparatus pumps blood from the vena cava into intake port 8. Optionally, balloon 2 is not inflated during pumping, or elements 2, 3, 4, and 4A are omitted from the apparatus (and the intake tubes consists of a continuous length of tubing extending from pump 9, through manifold 6, to distal end 8).

Return manifold 6 has an outer surface comprising outer cylindrical wall 6A and annular end walls 18 and 19. Tube 1B extends through the central openings of walls 18 and 19 (along the longitudinal axis of manifold 6), so that tube 1B and walls 6A, 18, and 19 surround (and define) a chamber 10 (shown in FIG. 3). Outer wall 6A is perforated by ports 17 and by a return tube port. Elbow fitting 11 (best shown in FIG. 1, and shown in a simplified view in FIG. 2) connects the distal end of return tube 5 to manifold 6 (at the return tube port which extends through wall 6A).

The proximal end of tube 5 is connected to an output port of pump 9. In operation, pump 9 pumps blood through return tube 5 at high pressure (substantially higher pressure than the pressure of blood in the intake tube) into fitting 11, and the blood flows from fitting 11 into manifold 6. More specifically, the blood flows from fitting 11 into the chamber 10 bounded by manifold 6's outer cylindrical wall 6A and end walls 18 and 19.

It may be desirable to configure the return lumen (e.g., the return lumen defined by elements 5, 11, and 6 in FIG. 2) to optimize the flow characteristics of blood flow therethrough, for example by minimizing turbulent flow (and thus any blood damage caused by turbulent flow) through the return lumen.

Intake tube (1A, 1B) preferably has larger diameter than does return tube 5 (as shown in FIG. 1). Since the blood in chamber 10 of manifold 6 has high pressure, it flows out into the right atrium from manifold 6 through return ports 17. At least one port 17 (and preferably multiple ports 17 as shown in FIGS. 1–3) extends (extend) through the outer cylindrical wall 6A of manifold 6.

Small-diameter tube 7, in fluid communication with chamber 10, extends out from manifold 6. Pressure sensor 16 (shown in FIG. 1) is coupled to the free end (the proximal end) of tube 7 for measuring the pressure of blood in chamber 10 (and thus the pressure of the blood which flows out from the inventive apparatus through ports 17 into the right atrium). Preferably, the stroke volume of pump 9 (the volume of blood flow through the pump during each cycle of pump operation) is controlled in response to the measured atrial outflow pressure (the output of sensor 16), to achieve a desired atrial pressure as a function of time. Preferably, the distal end of tube 7 does not extend significantly into chamber 10 (and does not otherwise disrupt blood flow within chamber 10). This is true since any blood flow disruption caused by the presence of tube 7 may generate clot (or otherwise damage the flowing blood).

Alternatively, where the apparatus returns blood to the right ventricle (rather than to the right atrium), a pressure sensor is coupled to the free end of a tube (corresponding to tube 7) for measuring the pressure of blood in chamber 10 (or a chamber corresponding to chamber 10) and thus the pressure of the blood which flows out from the inventive apparatus through return ports into the right ventricle).

Figure 4:
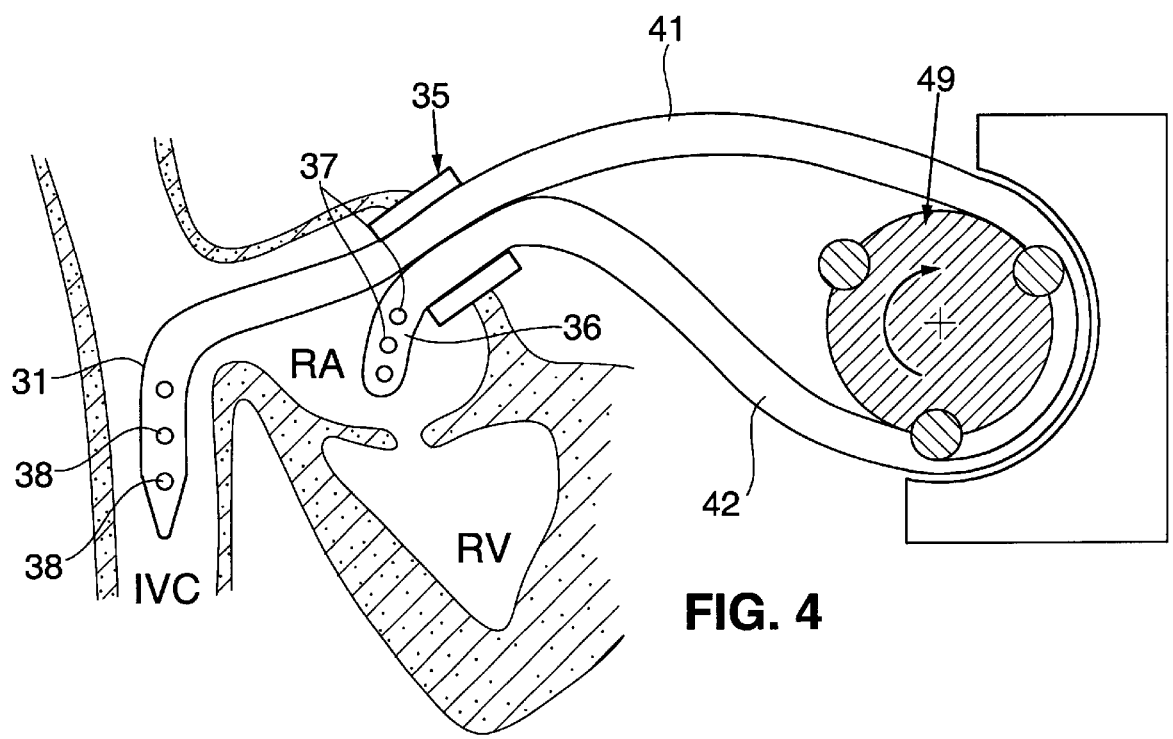
FIG. 4 is a simplified view (partially elevational and partially cross-sectional) of an alternative embodiment of the inventive apparatus.

Pump 9 can be a peristaltic pump, as such as peristaltic pump 49 of the FIG. 4 embodiment. In the FIG. 4 embodiment, peristaltic pump 49 comprises a rotatable element whose radius varies with angle about its central axis (it has three equally spaced portions with large radius, as shown), and intake tube 41 and return tube 42 are portions of a continuous, flexible tube. As peristaltic pump 49 rotates about its central axis, it exerts periodically time-varying force on the continuous, flexible tube so as to force blood in one direction only (clockwise around the pump as shown in FIG. 4) from the pump's input port (at which intake tube 41 meets pump 49) to the pump's output port (at which intake tube 42 meets pump 49).

In use, collar 35 of the FIG. 4 apparatus is positioned in an incision in the right atrium. The distal end 31 of intake tube 41 is inserted through collar 35 into the heart until distal end 31 (perforated with intake ports 38) is positioned in the inferior vena cava (as shown in FIG. 4). The distal end 36 of return tube 42 is also inserted through collar 35 into the heart until distal end 36 (perforated with outlet ports 37) is positioned in the right atrium (as shown). As pump 49 operates, blood from the vena cava is drawn through ports 38 into tube 41, and pumped back (at higher pressure) through tube 42, and through ports 37 (of tube 42) into the right atrium. A peristaltic pump can provide constant pressure increase without check valves (which cause turbulence) or pressure spikes, and without the need for pacing (e.g., using an electrocardiograph signal to control the pump).

In other embodiments, the pump a centrifugal pump or syringe pump, or a pump of some other type. The pumping action is pulsatile in some embodiment, and continuous (or a combination of pulsatile and continuous) in other embodiments.

With reference again to the preferred embodiment of FIGS. 1–3, intake port 8 is configured to be positioned in the inferior vena cava when return manifold 6 is positioned in the right atrium. In alternative embodiments, the distal end of the intake tube of the inventive apparatus is configured so that its intake port is (or its intake ports are) easily positionable in the superior vena cava (when the return manifold is positioned in the right atrium).

Figure 5:
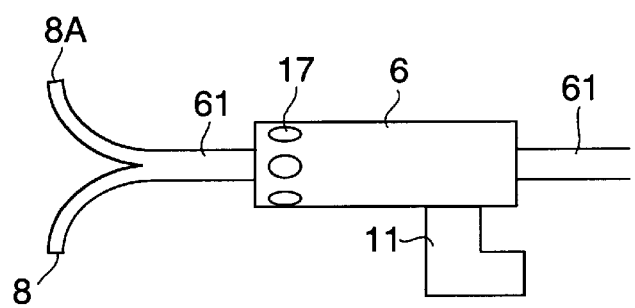
FIG. 5 is a simplified elevational view of part of another alternative embodiment of the inventive apparatus.

In other alternative embodiments (e.g., the embodiment of FIG. 5), the apparatus has an intake tube with a Y-shaped distal end having two intake ports (e.g., intake tube 61 of FIG. 5 which hag intake ports 8 and 8A of FIG. 5). Each intake port is configured to be positioned in a different one of the inferior vena cava and superior vena cava during use. In the FIG. 5 apparatus, blood pumped (by a pump not shown in FIG. 5) from both the inferior vena cava and superior vena cava (through intake tube 61) is returned to the right atrium (at increased pressure) through fitting 11 and return manifold 6, which correspond to identically numbered elements of the FIG. 1 apparatus.

Variations on the FIG. 5 apparatus include two separate intake tubes (one having one or more intake ports for positioning in the superior vena cava; the other having one or more intake ports for positioning in the inferior vena cava), both coupled to the pump.

Figure 6:
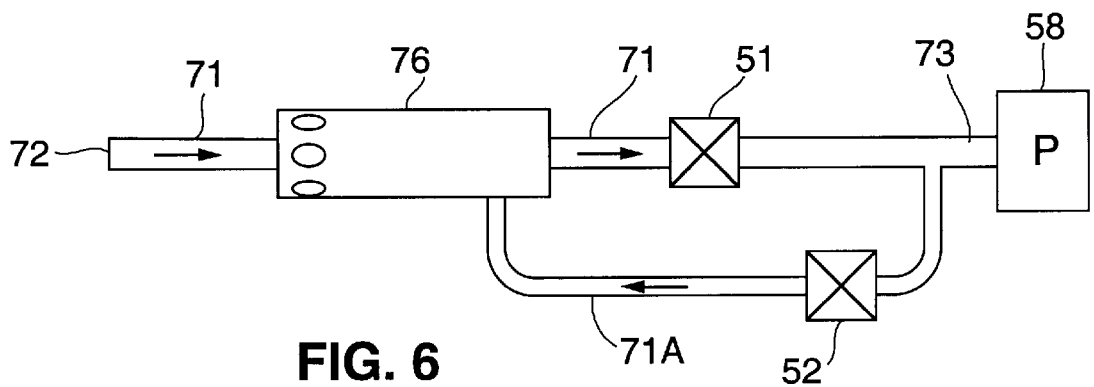
FIG. 6 is a simplified elevational view of another alternative embodiment of the inventive apparatus.

Another alternative embodiment of the invention will next be described with reference to FIG. 6. In this embodiment, the main branch of Y-tube 71 (having intake port 72 at its distal end) and return manifold 76 correspond functionally to the intake tube and return manifold of FIG. 1. The main (larger diameter) branch of intake tube 71 is optionally equipped with a fitting, balloon, and balloon inflation lumen corresponding functionally to elements 4, 2, and 3, respectively, of FIG. 1. However, return tube 71A is a small diameter branch of tube 71. Thus the intake and return tubes of FIG. 5 are branches of a single tube 71 having a Y-configuration (a "Y-tube"). Thus, pump 59 is connected at a single port (at proximal end portion 73 of the Y-tube) to both the return tube branch 71A and the main (intake tube) branch. One-way valve (check valve) 51 (connected along the main branch of tube 71) allows blood to flow (at low pressure) from intake port 72 to pump 59 but prevents backflow from pump 59 to port 72. One-way valve (check valve) 52 (connected along return tube branch 71A) allows blood to flow from pump 59 to return tube branch 71A but prevents backflow from return tube branch 71A to pump 59. Thus, pump 59 has one port (which functions as both an input port and an output port) and a two-stage cycle: a first stage in which it draws blood from proximal portion 73 of Y-tube 71 through the pump's port into the pump; and a second stage in which it returns blood from within the pump through the pump's port to proximal portion 73 of Y-tube 71, to cause the returning blood to flow through valve 52 into return tube branch 71A (but not through valve 51 to intake port 72). In some embodiments, the pump includes a piston which is retracted during the first stage and advanced in the second stage. In order to pace the pump 59 (i.e., achieve appropriate phase and frequency) during surgery on a beating heart, an electrocardiograph signal (indicative of the heart's functioning) is preferably used as a control signal for the pump.

Figure 7:
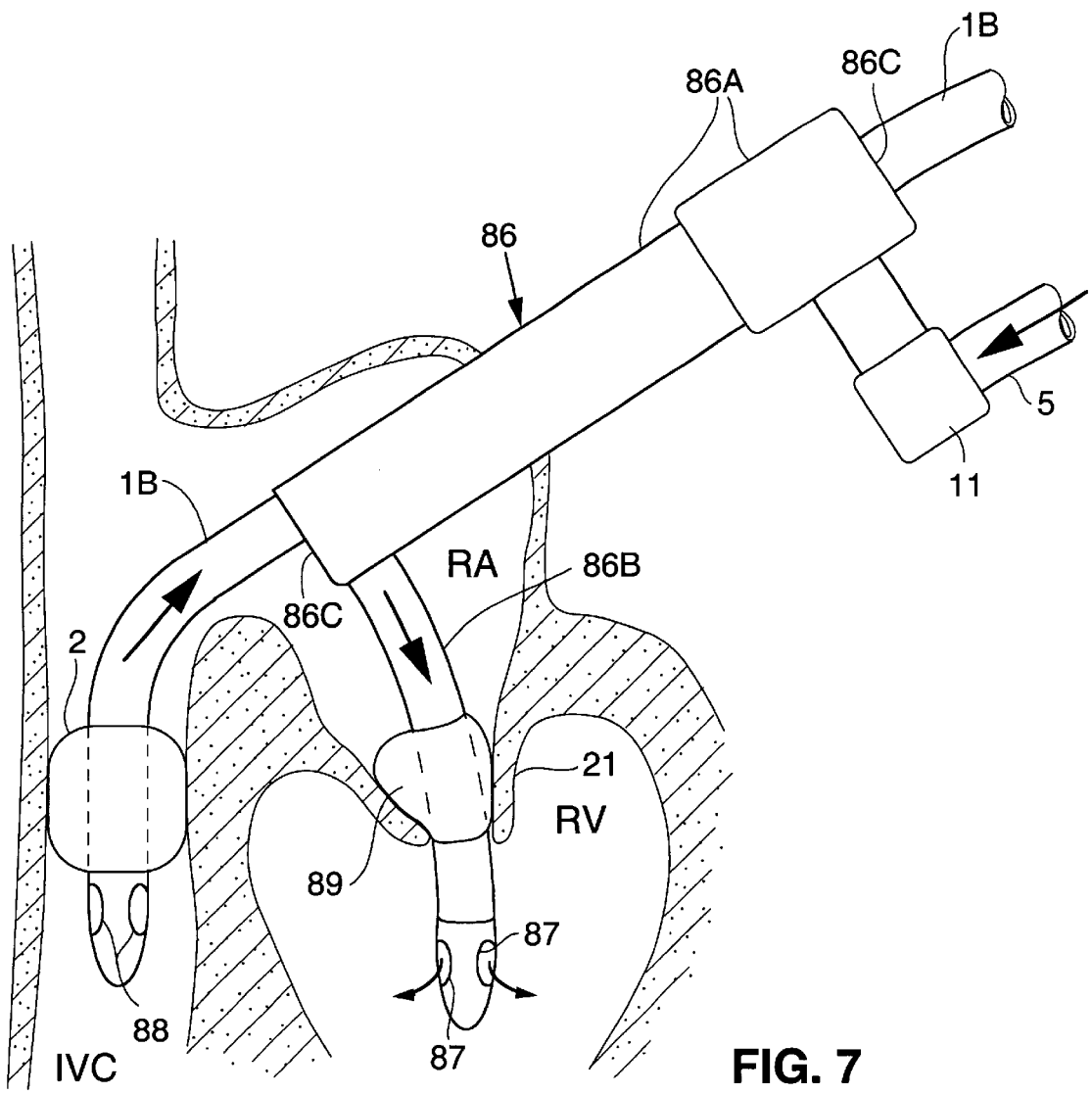
FIG. 7 is a simplified perspective view of a portion of an alternative embodiment of the inventive apparatus, elements of which are positioned in the right ventricle and inferior vena cava of a patient (the ventricle and vena cava are viewed in cross-section).

Another alternative embodiment of the invention will be described with reference to FIG. 7. In a variation on the embodiment of FIGS. 1–3, the FIG. 7 assembly replaces the assembly shown in FIG. 2. Identical components of the assemblies of FIGS. 2 and 7 are numbered identically in FIGS. 2 and 7. The FIG. 7 assembly differs from that of FIG. 2 as follows.

Intake ports 88 extend through the sidewall of tube 1B (near to tube 1B's closed distal end), so that intake ports can be inserted into the inferior vena cava. A balloon inflation lumen (not shown) extends along tube 1B and out through an orifice in the side wall of tube 1B (at a location under balloon 2, which location is thus not visible in FIG. 7) into fluid communication with the interior of balloon 2 so that fluid can be introduced or withdrawn through the lumen for inflating or deflating balloon 2 when desired. Balloon 2 is inflated (into the configuration shown in FIG. 7) when intake ports 88 have been inserted into the inferior vena cava, in order to provides a pressure bulkhead between the right atrium and the inferior vena cava, and preferably also to center the intake ports 88 in the inferior vena cava while the inventive apparatus pumps blood from the inferior vena cava into intake ports 88.

Return manifold 86 has an outer surface comprising outer cylindrical wall 86A and two end walls 86C. Each end wall 86C has an opening extending therethrough, and tube 1B extends through the openings in end walls 86C (along the longitudinal axis of manifold 86), so that tube 1B and walls 86A 86C surround (and define) a chamber. Outflow tube 86B has an open end coupled to wall 86A (so that the interior volume of tube 86B is in fluid communication with the mentioned chamber), and a closed end (dimensioned to be inserted from the right atrium through atrio-ventricular valve 21 into the right ventricle as shown). Tube 86B is perforated (near to its closed end) by return ports 87. In operation, a pump (e.g., pump 9 of FIG. 1) pumps blood through return tube 5 at high pressure into fitting 11, and the blood flows from fitting 11 into manifold 86, and out into the right ventricle through ports 87. More specifically, the blood flows from fitting 11 into the chamber bounded by outer cylindrical wall 86A, tube 1B, walls 86C, and tube 86B, and out into the right ventricle through ports 87. Since the blood in the chamber of manifold 86 is at high pressure, it flows out into the right ventricle (through return ports 87) and then flows beyond the right ventricle. At least one port 87 (and preferably multiple ports 87 as shown in FIG. 7) extends (extend) through the outer cylindrical wall of tube 86B.

The FIG. 7 apparatus also includes inflatable balloon 89. A second balloon inflation lumen (not shown, but distinct from the above-mentioned balloon lumen) extends along tube 1B, into tube 86B, and out through an orifice in the side wall of tube 86B (at a location under balloon 88 which location is thus not visible in FIG. 7) into fluid communication with the interior of balloon 89. Thus, fluid can be introduced or withdrawn through the second balloon inflation tube for inflating or deflating balloon 89 when desired. Balloon 89 is inflated (into the configuration shown in FIG. 7), when the distal end of tube 86B (including return ports 87) has been inserted from the right atrium, through the atrio-ventricular valve 21, and into the right ventricle, in order to prevent backflow of blood from the right ventricle into the right atrium during systole (by providing a pressure bulkhead) and to center the return ports 87 in the right ventricle, while the inventive apparatus pumps blood from tube 86B into the right ventricle through return ports 87.

One benefit of the FIG. 7 apparatus is that it completely bypasses the right atrium during manipulations that might otherwise severely impair the performance of the right atrium, such as the placement of a stabilizing foot directly on the right coronary artery.

In the various embodiments of the invention, the intake and return tubes, balloon or balloons (for backflow prevention and intake port centering), and return manifold can vary greatly with respect to size and materials. The maximum sizes of the invasive portions of the inventive apparatus are limited by patient anatomy, but the intake tube typically will not exceed one half inch in outside diameter, the centering balloon (at the distal end of the intake tube) typically will not exceed two inches in inflated diameter, and the return manifold typically will not exceed one inch in outside diameter. In typical embodiments, the materials for the intake and return tubes, balloons, and return manifold will be polymeric. At least those portions of the inventive apparatus in contact with patient tissue (the heart or vena cava) during use are preferably smooth and flexible, to avoid trauma to the tissue during positioning and operation of the apparatus.

It is contemplated that in preferred embodiments, the interior (blood-contacting) surfaces of the apparatus (including return and intake tubes, manifold, and pump) are heparin coated (or otherwise treated to prevent blood clot formation thereon (and to prevent blood clot formation in or on the apparatus).

The foregoing is merely illustrative and explanatory of preferred embodiments of the inventive methods and apparatus. Various changes in the component sizes, materials, and shapes, and other details of the embodiments described herein may be within the scope of the appended claims. For example, the distal end of tube 1B (of FIGS. 1 and 2) can define multiple blood intake ports (rather than a single intake port 8), and return manifold G can define a single return port 17 (rather than multiple return ports 17 as indicated in FIGS. 1 and 2).

What is claimed is:

1. An apparatus for assisting cardiac function of a heart having a right atrium, a right ventricle, an inferior vena cava, and a superior vena cava connected to the superior vena cava, said apparatus comprising:

an intake tube having a distal portion which defines at least one intake port, wherein the distal portion is configured to be positioned in at least one of the inferior vena cava and the superior vena cava to allow blood to flow into the intake tube through the at least one intake port from said at least one of the inferior vena cava and the superior vena cava;

a return assembly having a distal portion which defines at least one return port; and a pump, coupled between the intake tube and the return assembly and configured to pump the blood from the intake tube to the return assembly, wherein the blood has a first average pressure in the intake tube and an average pressure greater than the first average pressure in the return assembly, and the distal portion of the return assembly is configured to be positioned in one of the right atrium and the right ventricle when the distal portion of the intake tube is positioned in said at least one of the inferior vena cava and the superior vena cava, thereby allowing the blood in the return assembly to flow through the at least one return port into said one of the right atrium and the right ventricle, wherein the return assembly comprises:

a manifold at the distal portion of the return assembly, wherein the manifold has an outer surface perforated by the at least one return port and by a return tube port, and wherein the intake tube passes through the manifold; and a return tube coupled between the pump and the return tube port of the manifold, whereby blood can flow from the pump through the return tube into the manifold and out from the manifold through said at least one return port.

2. The apparatus of claim 1, wherein the manifold, the intake tube, and the return tube are made of polymeric material.

3. The apparatus of claim 1, wherein blood-contacting surfaces of the manifold, the intake tube, the return tube, and the pump are treated to prevent blood clot formation thereon.

4. The apparatus of claim 3, wherein blood-contacting surfaces of the manifold, the intake tube, the return tube, and the pump are heparin coated.

5. The apparatus of claim 1, wherein blood-contacting surfaces of the manifold, the intake tube, the return tube, and the pump are shaped to minimize turbulent blood flow.

6. The apparatus of claim 1, also comprising an atrial pressure sensor assembly, said atrial pressure sensor assembly comprising:

a tube having a first end in fluid communication with the manifold and a second end; and a pressure sensor coupled to the second end of the tube.

7. An apparatus for assisting cardiac function of a heart having a right atrium, a right ventricle, an inferior vena cava, and a superior vena cava connected to the superior vena cava, said apparatus comprising:

an intake tube having a distal portion which defines at least one intake port, wherein the distal portion is configured to be positioned in at least one of the inferior vena cava and the superior vena cava to allow blood to flow into the intake tube through the at least one intake port from said at least one of the inferior vena cava and the superior vena cava;

a return assembly having a distal portion which defines at least one return port; and a pump, coupled between the intake tube and the return assembly and configured to pump the blood from the intake tube to the return assembly, wherein the blood has a first average pressure in the intake tube and an average pressure greater than the first average pressure in the return assembly, and the distal portion of the return assembly is configured to be positioned in one of the right atrium and the right ventricle when the distal portion of the intake tube is positioned in said at least one of the inferior vena cava and the superior vena cava, thereby allowing the blood in the return assembly to flow through the at least one return port into said one of the right atrium and the right ventricle, wherein the return assembly comprises:

a manifold at the distal portion of the return assembly, wherein the manifold defines a channel through which the intake tube passes; and a return tube connected between the pump and the manifold, wherein the manifold defines a chamber that is sealed from the intake tube but is in fluid communication with the return tube, and the chamber is perforated by the at least one return port, whereby blood can flow from the pump through the return tube into the chamber and out from said chamber through said at least one return port.

* * * * *